United States Patent [19]

Tobin

[11] 4,101,554
[45] Jul. 18, 1978

[54] CATALYTIC PROCESS FOR THE PREPARATION OF PERFLUOROALKYL-SUBSTITUTED HETEROCYCLIC COMPOUNDS

[75] Inventor: John H. Tobin, Winsted, Conn.

[73] Assignee: Olin Corporation, New Haven, Conn.

[21] Appl. No.: 791,362

[22] Filed: Apr. 27, 1977

Related U.S. Application Data

[63] Continuation-in-part of Ser. No. 643,227, Dec. 22, 1975, Pat. No. 4,038,331, which is a continuation-in-part of Ser. No. 549,589, Feb. 13, 1975, abandoned.

[51] Int. Cl.$^2$ .......................................... C07D 213/26
[52] U.S. Cl. ........................ 260/290 HL; 260/296 B; 260/296 D
[58] Field of Search ................................ 260/290 HL

[56] References Cited

U.S. PATENT DOCUMENTS 3,890,326   6/1975   Tobin ............................ 260/290 HL

OTHER PUBLICATIONS

Yagupol'skii et al., Chem. Abstracts, vol. 69, (15), Item No. 59,064-b, Oct. 7, 1968.
Yagupol'skii et al., Chem. Abstracts, vol. 70, (21), Item No. 96,632-b, May 26, 1969.
Yagupol'skii et al., Chem. Abstracts, vol. 72, (8), Item No. 31,676-r, Feb. 23, 1970.

Primary Examiner—Alan L. Rotman
Attorney, Agent, or Firm—William A. Simons; Thomas P. O'Day

[57] ABSTRACT

Process for the preparation of perfluoroalkyl-substituted heterocyclic compounds wherein perfluoroalkyl bromide is reacted with the heterocyclic substrate in a vapor phase under anhydrous conditions at temperatures from about 300° C to about 800° C in the presence of a catalytic amount of a catalyst selected from the group of iodine or an iodine generating compound.

9 Claims, No Drawings

CATALYTIC PROCESS FOR THE PREPARATION OF PERFLUOROALKYL-SUBSTITUTED HETEROCYCLIC COMPOUNDS

CROSS-REFERENCE TO RELATED APPLICATIONS

This application is a continuation-in-part application of co-pending U.S. patent application Ser. No. 643,227, filed Dec. 22, 1975, which was a continuation-in-part application of U.S. patent application Ser. No. 549,589, filed on Feb. 13, 1975, now abandoned.

BACKGROUND OF THE INVENTION

1. Field of the Invention

This invention relates to a method for preparing perfluoroalkyl-substituted heterocyclic compounds. More particularly, the invention relates to a method for preparing such compounds by reacting a perfluoroalkyl bromide with heterocyclic substrates in the presence of a catalytic amount of iodine or an iodine generating compound.

2. Description of the Prior Art

Perfluoroalkyl-substituted heterocyclic compounds are used today as chemical intermediates for many chemicals which are utilized as pesticides, herbicides, fungicides, bactericides and as anti-inflammatory and analgesic agents. In particular, U.S. Pat. No. 3,609,158, issued to Torba on Sept. 28, 1971, describes pesticidal and herbicidal derivatives of trifluoromethylpyridine. Further, U.S. Pat. No. 3,787,420, No. 3,787,422, and No. 3,787,425, all issued on Jan. 22, 1974, describe derivatives of trifluoromethyl pyridines which are utilized as fungicides and bactericides. Japanese Kokai 74/35,386, published by Maeda et al. on Apr. 1, 1974, shows trifluoromethyl pyridine derivatives as anti-inflammatory and analgesic agents. Compounds made by the present process may be utilized in making these types of derivatives.

In the past, perfluoroalkyl-substituted heterocyclic compounds were made by reacting perfluoroalkyl iodides (not bromides) with the heterocyclic substrate in the presence of a free radical generating compound such as organic peroxides and aliphatic azo compounds. U.S. Pat. No. 3,271,441, issued to Brace on Sept. 6, 1966, discloses such a process.

While perfluoroalkyl iodides have been used to prepare perfluoroalkyl-substituted heterocyclic compounds, efforts to utilize less expensive perfluoroalkyl bromides have been unsuccessful. U.S. Pat. No. 3,890,326, issued to the present inventor on June 17, 1975, shows that an uncatalyzed vapor phase reaction of a heterocyclic compound and trifluoromethyl bromide results only in the bromine substitution of a hydrogen on the heterocyclic ring, thereby producing fluoroform ($CF_3H$) and a brominated heterocyclic product. Virtually, no perfluoromethyl-substituted heterocyclic products were made by this method.

Therefore, a need exists for a process for making perfluoroalkyl heterocyclic compounds which can utilize as a reactant perfluoroalkyl bromides instead of the more costly perfluoroalkyl iodides. It is believed that the present invention satisfies this need.

SUMMARY OF THE PRESENT INVENTION

The present invention is directed to a process for producing perfluoroalkyl-substituted heterocyclic compounds by reacting together a perfluoroalkyl bromide and a heterocyclic substrate in a vapor phase under anhydrous conditions at a temperature from about 300° C to about 800° C in the presence of a catalytic amount of a catalyst selected from the group consisting of iodine and iodine generating compounds.

DETAILED DESCRIPTION

In accordance with the present invention, the reactants and catalyst are charged into a vapor phase reactor maintained at a temperature in the range of from about 300° C to about 800° C which has been previously purged with nitrogen or another inert gas to remove water vapor therefrom. The reaction is permitted to proceed under these conditions in accordance with the generalized reaction:

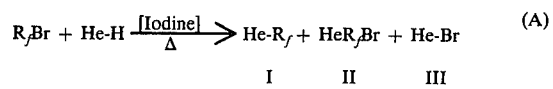

$$R_fBr + He\text{-}H \xrightarrow[\Delta]{\text{[Iodine]}} He\text{-}R_f + HeR_fBr + He\text{-}Br \quad (A)$$

$$\quad\quad\quad\quad\quad\quad\quad\quad\quad\quad\quad\text{I}\quad\quad\text{II}\quad\quad\text{III}$$

wherein $R_f$ represents a perfluoroalkyl moiety, He—H represents a heterocyclic substrate having an available ring hydrogen and [Iodine] represents iodine or an iodine generating compound, all described in detail below.

Suitable heterocyclic substrates that can be employed as reactants in the process of the present invention include those having from about 6 to about 10 ring atoms that consist of 1–3 atoms, preferably 1, of nitrogen with the balance being carbon atoms. There should be at least one hydrogen atom attached to one of the carbon ring atoms for substitution with the perfluoroalkyl group. Desirably, 0–3 of the ring carbon atoms may be substituted with an inert substituent such as fluoro, chloro, bromo, perfluoroalkyl, perchloroalkyl, perbromoalkyl, nitrile groups and combinations thereof.

These substituents are called inert because they will not react with the perfluoroalkyl bromide during the present process. The position of the inert substituents on the heterocyclic ring is not critical to the present invention and they may occupy any position relative to the nitrogen atom or atoms.

Preferably, the heterocyclic substrate may be substituted with 0–3 fluoro-, chloro- or bromo- groups or combinations thereof.

The heterocyclic substrate may be also substituted with 0–3 perfluoroalkyl, perchloroalkyl or perbromoalkyl groups in which the alkyl component of such a group has from 1 to about 4 carbon atoms, preferably 1 to about 2 carbon atoms, most preferably, 1 carbon atom. Typical examples of these perhaloalkyl substituents include $CF_3$, $C_2F_3$, $CCl_3$, and the like. The most preferred halogens of this group are fluorine and chlorine, although bromine may also be preferred in some situations.

From 0–3 nitrile groups can also be present on the heterocyclic substrate. The nitrile group can be alone or in combination with one or more fluoro-, chloro-, or bromo- groups or in combination with one or more perfluoroalkyl, perchloroalkyl, or perbromoalkyl groups or even in a combination of one of these halogroups and one of these perhaloalkyl groups.

The preferred heterocyclic substrates are single 6-membered rings containing one nitrogen atom atom and 5 carbon ring atoms such as pyridine or a substituted pyridine. However, other heterocyclic substrates which may be employed herein include unsubstituted or appropriately substituted pyridazines, pyrimidines, pyrazines, quinolines, isoquinolines, quinazolines, quinozalines, phthalazines, napththyridines, pyridopyridines, or purines.

Most preferred of the hetrocyclic substrates is unsubstituted pyridine or an appropriately monosubstituted pyridine. A preferred example of this latter group is 2-chloropyridine. Pyridine and its simple derivatives such as 2-chloropyridine are readily available on large commercial scales. Furthermore, perfluoromethyl pyridines are valuable intermediates for making many of the chemicals indicated in the patents cited above.

The second reactant of the present process is a perfluoroalkyl bromide wherein the alkyl component has from 1 to about 4 carbon atoms, more preferably 1 to about 2 carbon atoms, and most preferably is perfluoromethyl bromide. The molar ratio of the perhaloalkyl bromide to the heterocyclic substrate is not critical to the present invention and any suitable molar ratio may be utilized. Preferably, from about 0.5 to about 2 moles, more preferably about 1 mole perfluoroalkyl bromide, are employed per mole of the heterocyclic substrate. However, when the perfluoroalkyl bromide is employed as a carrier gas besides being a reactant, this molar ratio may be greater than 2:1.

The novel feature of the present invention resides in the use of an appropriate catalyst. In U.S. Pat. No. 2,957,031, referred to above, it was disclosed that the uncatalyzed vapor phase reaction of trifluoromethyl bromide with an aromatic compound produced a brominated aromatic compound. Virtually no fluoroalkylation occurred. Surprisingly, however, when the reaction is conducted in the presence of a catalytic amount of iodine or an iodine generating compound, then perfluoroalkylation occurs.

Suitable iodine generating compounds which may be used in lieu of iodine include those compounds which decompose at a temperature in the range of from about 300° C to about 800° C to form iodine in situ. These may include halogenated alkyl iodide and interhalogen compounds. For example, one may utilize a perfluoroalkyl iodide, advantageously a lower perfluoroalkyl iodide having from 1 to about 4 carbons, preferably trifluoromethyl iodide, or iodine containing interhalogens such as IBr or ICl. However, iodine is the preferred catalyst because of its lower cost than the iodine generating compounds mentioned above.

In conducting the present process, a catalytic amount of iodine or iodine generating compound is present during the reaction. Generally, the employment of a molar ratio of iodine or iodine generating compound to the heterocyclic substrate within the range of 1:250 to 1:10, more preferably in the range of 1:100 to 1:15, will be sufficient to constitute a minimum catalytic amount. However, precise upper and lower limits as to what constitutes a catalytic amount will vary according to the reactants, particular catalysts, and other reaction parameters.

The reaction is carried out in a reactor heated at a temperature in the range of about 300° C to about 800° C, preferably from about 500° C to about 750° C, more preferably, from about 600° C to about 700° C. If the reaction temperature is above 800° C, decomposition of the reactants and desired products is likely to occur. If the reaction temperature is below about 300° C, then the reaction time may be unduly long and/or the heterocyclic substrate may not be sufficiently vaporized.

The present reaction is carried out in the vapor phase because at these elevated temperatures both reactants and the catalyst are in the gaseous state. Furthermore, the reaction should not be carried out in the presence of water because water can react with the trifluoroalkyl bromide and possibly the desired products thereby causing lower product yields. Thus, it is necessary to carry out the reaction under anhydrous (i.e., substantially water-free) conditions. This can be easily accomplished by purging the reactor before the introduction of the reactants and catalyst with an inert gas such as nitrogen, helium, or the like.

The reaction is allowed to proceed for a period of at least one minute up to several (6–10) hours depending on the temperature, the specific reactants which have been selected and on the degree of completion required for the reaction. The optimum residence time in the reactor may be readily determined by those skilled in the art and will vary with each particular reaction system.

Other than the critical reaction parameters mentioned above, it is believed there are no other necessary reaction conditions which must be followed in order to get the desired perfluoroalkyl-substituted heterocyclic compounds. For example, no particular pressures are necessary for obtaining the desired products. Atmospheric pressure is most preferred because there is no cost for pressurized equipment involved. However, it may be preferable for certain commercial advantages to use either above-atmospheric or below-atmospheric pressures. Furthermore, it may be desirable to employ an inert carrier gas such as nitrogen, helium, or the like to facilitate recovery of the product and/or the reactants.

The reaction mechanism of the present process is not exactly known, however, it is theorized that the perfluoroalkyl bromide forms two free radicals ($C_NF_{N+2}$· and Br·) at these elevated temperatures in the presence of iodine or an iodine generating compound. These two free radicals can each substitute with a hydrogen on the heterocyclic substrate. As shown in Equation (A) above, the present reaction forms as products various isomers of two perfluoroalkyl-substituted heterocyclic compounds (I) and (II) and isomers of a purely brominated compound (III). Because of these differing physical properties such as molecular weights, boiling point, and the like, these various products can be easily separated. Both compounds (I) and (II) may be valuable intermediates for other chemicals. The term "perfluoroalkyl-substituted heterocyclic compound" as used herein includes all isomers of both types of compounds.

After the reaction is completed, the products can be recovered by any conventional purification or chemical isolation procedure. Repeated distillation of the product mixture may be one desired means of isolating the particular perfluoroalkyl-substituted compounds.

The following examples are presented to further illustrate the invention without any intention of being limited thereby. All parts and percentages are by weight unless otherwise specified.

EXAMPLE I

A vapor phase reactor was constructed of quartz and consisted of three sections. Section I was a series of valves permitting the introduction of one gas and a liquid in measured quantities. Section II was a reactor tube 24 inches long and 1 inch in diameter and packed with an inert support. Section III is a trap system to trap the product mixture using a cold finger filled with ice water/alcohol bath.

A liquid solution of 9.6 gms $I_2$ and 90.4 gms pyridine was prepared (a 1:30 molar ratio of $I_2$ to pyridine). The reaction tube was heated to approximately 600° C under a nitrogen purge. When the temperature stabilized the nitrogen flow was stopped.

The liquid $I_2$ and pyridine solution were introduced into the reaction tube at a rate of about 0.8 ml per minute. Simultaneously, trifluoromethyl bromide gas was introduced into the reaction tube at a rate of about 60–80 ml per minute. This gas functioned as a carrier gas for the system besides being reactant.

Product was collected from the trap and analyzed by vapor phase chromatography, infrared spectroscopy, and mass spectroscopy. It was determined that from this single-pass reaction that 2.5% by weight of the pyridine was converted into reaction products. Of these products, 27% by weight was trifluoromethyl pyridine, 42% by weight was bromotrifluoromethyl pyridine and 10% by weight was bromopyridine for a total yield of 79% by weight based on the amount of pyridine converted. No determination of the various isomers of these products was made.

This example demonstrates that the reaction of a perfluoroalkyl bromide with heterocyclic substrate in the presence of an appropriate catalyst results in significant fluoroalkylation of the heterocyclic ring.

EXAMPLE II

The same apparatus and procedure as used in Example I were followed except a reaction temperature of approximately 650° C was used. This resulted in 7.0% by weight conversion for a single-pass reaction of pyridine substrate. Upon analysis, it was determined that the product mixture was 25% by weight trifluoromethyl pyridine, 41% by weight bromotrifluoromethyl pyridine and 16% by weight bromopyridine for a total yield of 82% by weight based on the amount of pyridine converted.

EXAMPLES III–V

The apparatus and procedure of Example I were followed except a liquid solution of 13.8 gms $I_2$ and 86.2 gms pyridine was utilized (this is 1:20 molar ratio of $I_2$ to pyridine). Further, the reaction temperature was varied for each of these examples.

Temperature, conversion of pyridine, and yields based on the pyridine converted as corresponding to Example I are presented in Table I below:

TABLE I

| Ex. | Temp. °C | Conversion of Pyridine | Yields | | | |
|---|---|---|---|---|---|---|
| | | | $CF_3Py$ | $BrCF_3Py$ | BrPy | Total |
| III | 600 | 4.8 | 28 | 42 | 20 | 90 |
| IV | 650 | 7.9 | 29 | 45 | 16 | 90 |
| V | 700 | 13.0 | 21 | 43 | 24 | 88 |

EXAMPLES VI–VII

The apparatus and procedure of Example I were followed except that 2-chloropyridine was used instead of pyridine. Furthermore, a liquid solution of $I_2$ and 2-chloropyridine was prepared by combining 10.0 gms $I_2$ with 90.0 gms of 2-chloropyridine (1:20 molar ratio of these two reactants).

Table II shows the temperatures employed, conversions of 2-chloropyridine and yields based on the 2-chloropyridine converted.

TABLE II

| Ex. | Temp. °C | Conversion of 2-Cl Pyridine | Yields | | | |
|---|---|---|---|---|---|---|
| | | | $ClPyCF_3$ | $ClPyBrCF_3$ | ClPyBr | Total |
| VI | 650 | 6.9 | 38 | 43 | 12 | 93 |
| VII | 700 | 11.0 | 39 | 50 | 12 | 101 |

What is claimed is:

1. A process for preparing perfluoroalkylsubstituted pyridines which comprises
   a. heating together in the vapor phase under anhydrous conditions at temperatures from about 300° C to about 800° C
      (1) a pyridine compound containing at least one hydrogen atom attached to a ring carbon atom and further substituted with from 0 to about 3 inert substituents;
      (2) a perfluoroalkyl bromide having from about 1 to about 4 carbon atoms; and
      (3) a catalytic amount of a catalyst selected from the group consisting of iodine and an iodine generating compound selected from the group consisting of perhaloalkyl iodine having 1 to 4 carbon atoms, IBr, and ICl.

2. The process of claim 1 wherein said pyridine is 2-chloropyridine.

3. The process of claim 1 wherein said inert substituents are selected from the group consisting of fluorine, chlorine, bromine, perfluoroalkyl having 1 to about 4 carbon atoms, perchloroalkyl having 1 to about 4 carbon atoms.

4. The process of claim 3 wherein said perfluoroalkyl bromide is perfluoromethyl bromide.

5. The process of claim 3 wherein said catalyst is iodine.

6. The process of claim 3 wherein said perfluoroalkyl bromide has from 1 to 2 carbon atoms.

7. The process of claim 6 wherein said catalyst is iodine.

8. The process of claim 7 wherein said pyridine is unsubstituted pyridine or a mono-substituted pyridine and said perfluoroalkyl bromide is perfluoromethyl bromide.

9. The process of claim 8 wherein said reaction temperature is from about 600° C to about 700° C.

* * * * *

UNITED STATES PATENT AND TRADEMARK OFFICE
CERTIFICATE OF CORRECTION

PATENT NO. : 4,101,554
DATED : July 18, 1978
INVENTOR(S) : John H. Tobin

It is certified that error appears in the above-identified patent and that said Letters Patent are hereby corrected as shown below:

In Column 6, line 44, after "atoms" insert --, perbromoalkyl having 1 to about 4 carbon atoms, nitrile and combinations thereof.--.

Signed and Sealed this

Sixth Day of March 1979

[SEAL]

Attest:

RUTH C. MASON
Attesting Officer

DONALD W. BANNER
Commissioner of Patents and Trademarks